(12) United States Patent
Schulz

(10) Patent No.: US 8,491,666 B2
(45) Date of Patent: Jul. 23, 2013

(54) FINGER ELEMENT

(76) Inventor: Stefan Schulz, Karlsruhe (DE)

( * ) Notice: Subject to any disclaimer, the term of this patent is extended or adjusted under 35 U.S.C. 154(b) by 145 days.

(21) Appl. No.: 13/203,616

(22) PCT Filed: Nov. 4, 2009

(86) PCT No.: PCT/DE2009/001537
§ 371 (c)(1),
(2), (4) Date: Aug. 26, 2011

(87) PCT Pub. No.: WO2010/051798
PCT Pub. Date: May 14, 2010

(65) Prior Publication Data
US 2012/0109337 A1    May 3, 2012

(30) Foreign Application Priority Data
Nov. 8, 2008 (DE) .......................... 10 2008 056 520

(51) Int. Cl.
*A61F 2/54* (2006.01)
*A61F 2/70* (2006.01)

(52) U.S. Cl.
USPC .............................................. 623/24; 623/64

(58) Field of Classification Search
CPC .................. A61F 2/586; A61F 2002/586; A61F 2005/0155; B25J 15/0009; B25J 15/0213; B25J 15/024; B25J 15/12
See application file for complete search history.

(56) References Cited

U.S. PATENT DOCUMENTS
2009/0145254 A1*  6/2009  Hirabayashi et al. ........... 74/425

FOREIGN PATENT DOCUMENTS

| EP | 0748194 | 7/1998 |
|---|---|---|
| GB | 3023680 | 1/2006 |
| WO | 2007/063266 | 6/2007 |
| WO | 2007/076764 | 7/2007 |
| WO | 2010/051798 | 5/2010 |

OTHER PUBLICATIONS

Girard Transmissions, "Motor Technology-Girard gearboxes", extract from BR Series handbook, Dec. 1998.
Bill Christensen "iLimb Bionic Hand Now Ready for Market", extract from Technovelgy.com, Sep. 12, 2012.
No author, "World's first bionic hand factory opened by Scottish company", extract from Daily Mail website http://www.dailymail.co.uk/sciencetech/article-506661/Worlds-bionic-hand-factory-opened-Scottish-company.html, Jan. 2008.

(Continued)

Primary Examiner — David H Willse
(74) Attorney, Agent, or Firm — Renner, Otto, Boisselle & Sklar, LLP

(57) ABSTRACT

The invention relates to a finger element, comprising a carrier component (1), a first finger member (5) having a first articulated connection (2) to the carrier component, a second finger member (6) having a second articulated connection (7) to the first finger member, an actuator for the first articulated connection (2) with a motor having a drive shaft, and a worm gear having a threaded worm, and a toothed segment engaging on the threaded worm, and further comprising a coupling mechanism (8) between the first and second articulated connections. The object of the invention is to modify a finger element such that the finger element in the active and passive functions thereof and in the dimensions thereof comes very close to a natural finger. The object is achieved in that the threaded worm is positively mounted axially movably on the drive shaft and axially guided through separate guides.

11 Claims, 3 Drawing Sheets

OTHER PUBLICATIONS

Jonathan Fildes, "Bionic hand wins top tech prize", extract from BBC News website http://news.bbc.co.uk/2/hi/sci/tech/7443866.stm, Jun. 2008.

International Search Report corresponding to International Application No. PCT/DE2009/001537, dated Mar. 22, 2010.

* cited by examiner

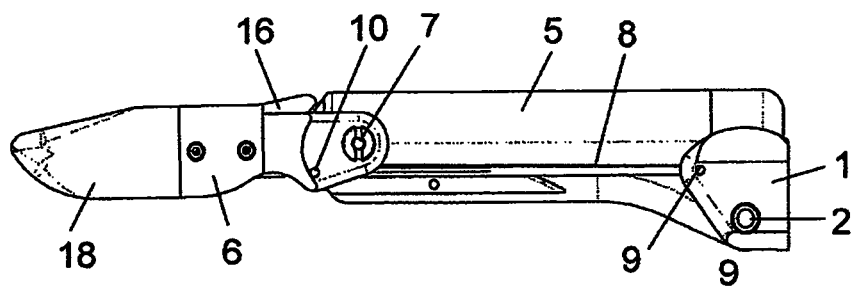
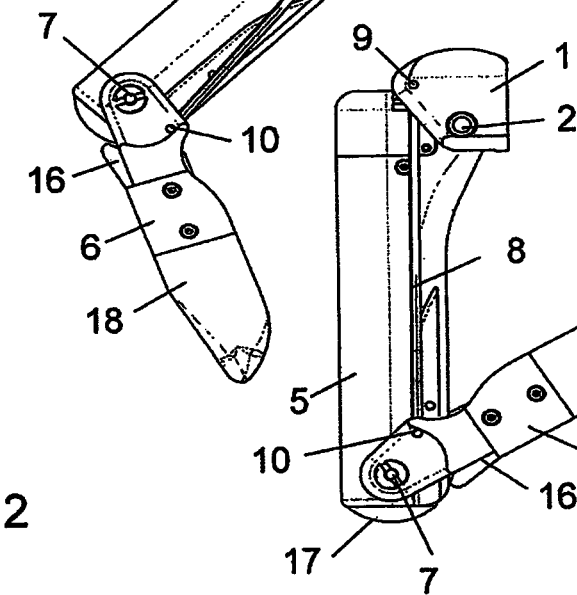
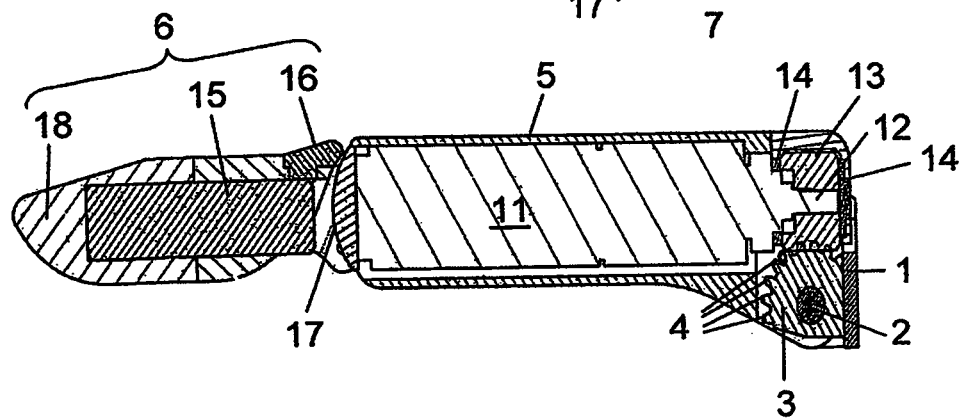

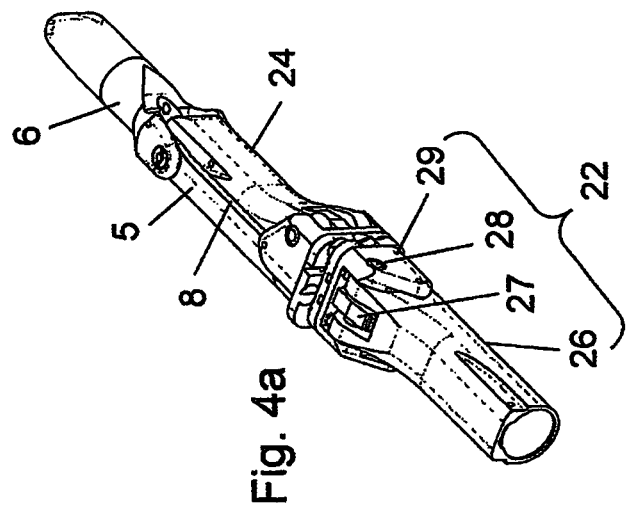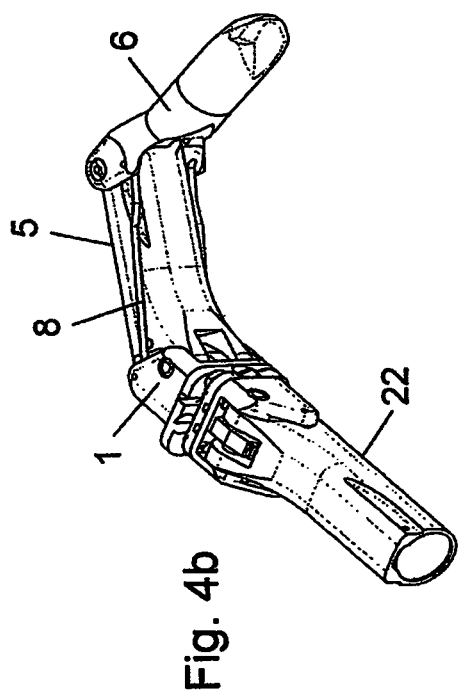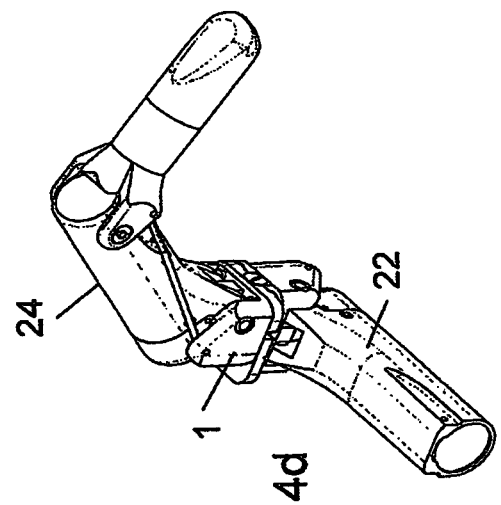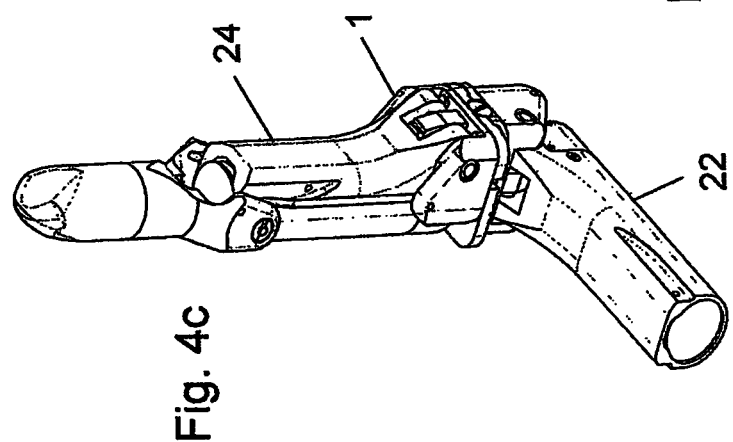

FINGER ELEMENT

TECHNICAL FIELD

The invention relates to a finger element according to the first claim. It serves as autarkic element for the use as artificial single-finger-prosthesis or as component of an artificial hand- or arm-prosthesis.

BACKGROUND ART

Artificial finger elements are available which can be used as integral parts of hand- or arm-prostheses. They orientate in their form and its motility to a finger.

From DE 309 367 hand-prostheses with multi-member thumb- and forefinger-elements, that work against each other, are already known from the time of the First World War. The single finger joints are positioned via a gearing with tooth sector and threaded screws, wherein the drive is carried out via cable pulls and lever mechanisms out of the thenar. A motoric drive is not envisaged, as well as an individual motility of single fingers.

Even the DE 323 970 dated 1919 discloses such a rotation mechanism for a phalanx.

Hand-prostheses with a motoric rotation drive for two fingers against each other are disclosed for instance by DE 26 07 499 C3 and U.S. Pat. No. 4,094,016. A geared motor as control member is arranged in these concepts in the thenar-area of the prosthesis.

However, the mentioned systems do not enclose any autarkic driven finger elements, wherein all control members which are necessary for the operation are enclosed in the finger element. The drives in these systems arranged outside the finger elements. Thus, they are conceptually not suited for the use as single-finger-prosthesis. Also the use as component in a prosthesis-modular-system is substantially restricted by that.

In contrary, the DE 698 16 848 T2 as well as the DE 198 54 762 C2 respectively disclose a finger element, each with a motoric rotation drive with a threaded screw and a gearing per hinge. The motors are arranged directly in the phalanges.

However, in these finger elements, the worm gear is fixed permanently to the motor shaft, such that in case of an applied load of the finger element high forces may affect the motor. An early drive- or motor-damage as well as a blocking of the worm drive under load is abetted therewith.

Constructions as described for instance in DE 319 092 A and US 2005 0021154 A1, wherein the movements of the distal phalanges may be achieved via stiff push- and pull-rods which are all but not elastic, appear mostly to be unrealistically robot-like and are not suited in particular for sensitive picking problems. Also in this case early overload symptoms have to be expected.

In contrary, in WO 2007/063266 A1 a hand-prosthesis with moveable finger elements is described, wherein a decoupling of drive shaft and threaded screw is realized via a bevel gear transmission arranged in between with a direction change of the rotation movement of about a right angle.

With the latter concept a mechanic partial decoupling of worm wheel and drive shaft and therefore a mechanic load revealing of the last named is disclosed, but in connection with additional components and/or a larger construction volume. The construction volume limits the use as single-finger-prosthesis in particular for the replacement of smaller fingers enormously by esthetic reasons.

BRIEF SUMMARY OF THE INVENTION

On this basis it is the problem of the invention, to modify a finger element in a way, so that it is generally usable as an autarkic element that means also as single-finger-prosthesis. In particular, the finger element may be in its active and passive function as well as in its dimensions close to a natural finger, in particular also very close to smaller fingers and thereby comprise a long lifetime.

The problem is solved by a finger element with the features of claim 1. The sub-claims, which are referred back to claim 1 describe advantageous embodiments of the finger element.

The problem is solved by a finger element with a carrier component, a first phalanx that is articulated thereon via a first hinge connection as well as a second phalanx that is articulated via a second hinge connection to the first phalanx. Furthermore, a servo drive is envisaged for the first hinge connection. This servo drive encloses a motor with or without integrated gear transmission to a drive shaft. The drive shaft drives a threaded screw of an advantageously self-locking worm gear that in return engages in a cog segment and moves it synchronously to the rotation movement of the drive shaft. In addition, the finger element includes a coupling mechanism between the first and second hinge connection.

The cog segment is preferably a part of a gear or gear segment around a gear axis that preferably coincides at the same time with the rotation axis of the first hinge connection. The invention includes in general also a cog segment as part of a tooth bar that is moveably supported spaced apart from the rotation axis and engaging in the finger element.

An essential feature of the invention encloses a decoupling of drive shaft and threaded screw in axial direction to the drive shaft. The threaded screw is preferably attached to the drive shaft and is in rotation direction form-fittingly coupled to the drive shaft, for instance via a cogging or a matched joint. Therefore, the axial movability of the drive shaft in the threaded screw has to be assured.

Thus, the motor does not serve via the drive shaft as axial guidance of the threaded screw, but separate guidances. They are arranged preferably in form of sliding guidances at both front edges of the threaded screw.

It proved to be advantageous, to combine the guidances and the threaded screws to an assembly. For instance, both guidances are realized by a stiff preferably single-part frame, in which the screw is inserted with a small axial play.

When this assembly is inserted as a unit and/or the cog segment is in addition elastically flexible inserted in the finger element, an elastic bending resilience of the finger element around the hinge connection results by them that comes close to a functional replication of a natural finger. Preferably the named assembly is inserted therefore into an elastomeric holder in the finger element that makes a resilience of the assembly possible in lateral and/or rotatory degrees of freedom. The cog segment, the gear segment or the gear is preferably supported freely rotating on the rotation axis and is therefore elastically curbed in its rotation movement via its elastomeric elements.

In order to ensure a constant play between threaded screw and cog segment preferably a spacer is envisaged between rotation axis and the forenamed assembly. This spacer is preferably supported rotatably on the rotation axis and connected with the rotation axis of the threaded screw. Therefore, for instance the threaded screw is in its guidances and not only supported in axial direction but also in radial direction, whilst the spacer is fixed permanently with the guidances.

In case of an elastic resilience of the assembly and therefore the threaded screw relative to the motor, the form-locking support of the threaded screw on the drive shaft has to be envisaged as pivotable rotating joint, for instance as hinge shaft coupling for instance with circumferential solid-bodies, for instance balls of a ball ring, that engage in cavities of the drive shaft and internal bores of the threaded screw.

The coupling mechanism encloses preferably at least one elastic connection, for instance in form of a pull- and push-rod between the carrier component and the second phalanx in parallel to the first phalanx. The coupling mechanism consists further preferred of one or two spring bar connections (for instance spring wire or spring steel sheet) that engage eccentrically to the rotation axes of the first and second hinge connections to the respectively adjacent carrier components and second phalanx respectively. For the replication of the characteristics of a natural hand, that means with an elastic resilience with preferably in the beginning progressive spring characteristic, it proved as advantageous, to form the wire connections in a curved or buckled manner. It is in accordance with the mechanic of a natural finger, when the pull- and push-rod in closing direction (for instance for picking) is tensile loaded, and therefore is not only able to transmit higher forces, but also comprises a stronger progression in the spring characteristics (a curve or buckle in a spring bar connection is pulled straight when it is tensile loaded and thus becomes more stiff in contrary to a compressive loading).

BRIEF DESCRIPTION OF THE DRAWINGS

In the following, the invention will be explained with the help of example embodiments with the following figures.

FIG. 1a to c each show a side view of an embodiment in craned (a) as well as in two flexed (b, c) positions, FIG. 2 shows a principle sectional view of the embodiment in craned position, FIGS. 3a and b each show a view of a hand-prosthesis equipped with finger elements, as well as FIG. 4a to d each show a view of an embodiment as thumb-element in different positions.

DETAILED DESCRIPTION OF THE INVENTION

Figure 3A:
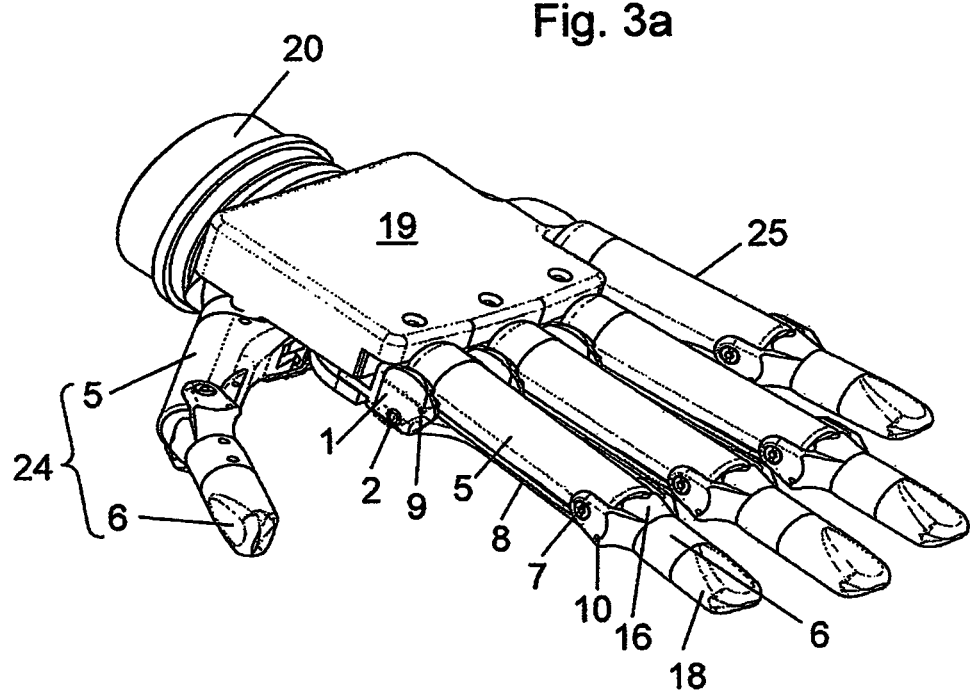
Figure 3B:
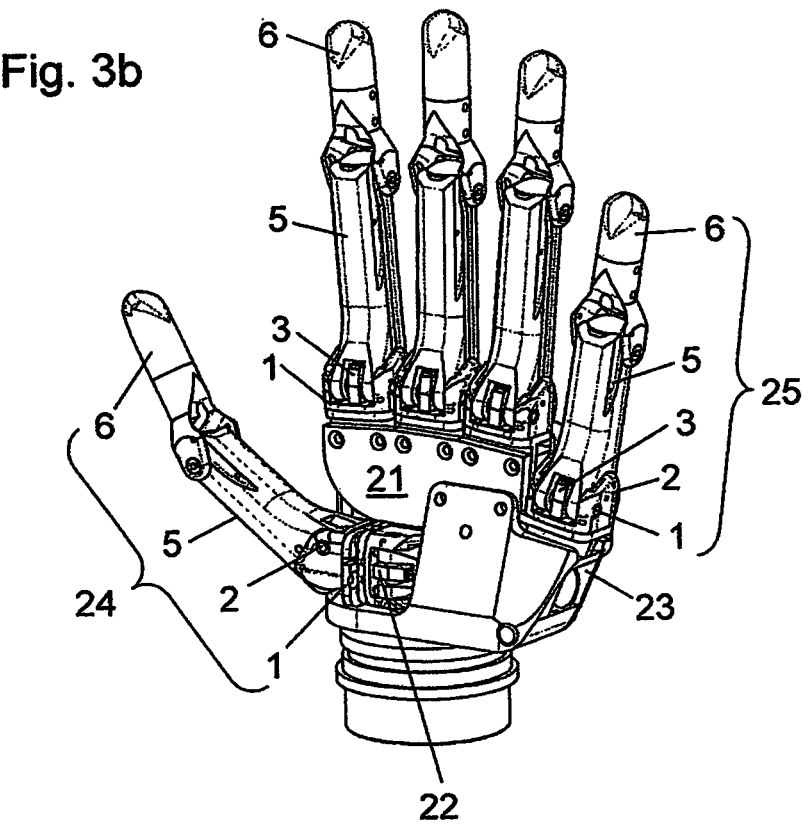

The shown embodiments of the finger element enclose each a carrier component 1 with a first hinge axis 2 and gear segment 3 with several cog segments 4. The carrier component 1 comprises not further explained means like mounting holes for the fixation of the finger elements for instance at a hand-prosthesis (cf. FIGS. 3a and b). The first hinge axis 2 serves at the same time as support of the gear segment and as rotation axis for the first phalanx 5. The first phalanx 5 is in return connected with the second phalanx 6 via a second hinge connection, wherein the second hinge axis 7 forms the rotation axis for the second phalanx. The rotation movement of the first and second phalanges around the according rotation axes is coupled via a coupling mechanism (cf. FIG. 1a to c and FIG. 4a to d). This coupling mechanism encloses in the example embodiments two elastic spring bar connections 8 that are arranged in parallel to each other at both sides of the first phalanx 5, wherein the spring bar connections 8 each engage at the carrier component and at the second phalanx pivotably in an according bearing bore 9 and 10 respectively eccentrically to the first 2 and second 7 hinge axis respectively.

FIG. 2 shows a sectional view of a finger element. A motoric drive ii for a threaded screw 13 that is directly attached to the drive shaft 12 is arranged inside a pipe-shaped first phalanx 5. The threaded screw is connected to each other via a not further explained key-slot-connection in rotation direction form fittingly, but axially movable pushed onto the drive shaft. The threaded screw is in the embodiment guided in radial direction onto the drive shaft, but is limited in its axial movability by two guidances 14 preferably without play. The materials of the threaded screw comprise in comparison to the materials of the guidances preferably a low sliding friction coefficient as well as high abrasive durabilities. For instance the threaded screw is because of the expected high load of the servo drive made of brass or steel, the guidances are preferably made of dry lubricating slide bearing bushing material like a PTFE-material or a slide bearing bronze.

The drive 11 encloses at least an electric motor as servo member, optionally also a gearing unit and/or for a use for instance as autarkic finger-prosthesis an electric voltage source as well as control electronics (battery, accumulator etc.), wherein in particular the latter components may be also arranged in the core 15 of the second phalanx 6.

The second phalanx 6 encloses in addition an elastic fingertip 18 preferably made of an elastomer as well as a deflector 16 that affects a slide face 17 of the first phalanx 5 (preferably an insertable lid element for instance made of plastics).

It proved to be advantageous, to integrate an optional tactile sensor into the fingertip 18 and/or into the core 15 and/or to attach resistance strain gauges to one of the phalanges, which directs or direct respectively a tactile signal directly to the control electronics (then preferably arranged in the core). The tactile signal preferably serves for the sensitive detection of an affecting force and for a tactile feedback of a picking force to the carrier of the prosthesis (force feedback) alternatively or in addition to the current drain of the motoric drive and therefore the force limitation of the movement control.

FIGS. 3a and b show a hand-prosthesis with a rotatable link component 20, thenar element 19 (FIG. 4a) and several finger elements in the described embodiment in two perspectives. All finger elements are fixed via the carrier component to the thenar element 19. Forefinger-, middle-finger- and ring-finger-element are therefore stiffly attached to an elastic adaptor 21 (FIG. 4b) whereas a separate finger element adaptor 22 is envisaged with an additional hinge, that is actively driven that is designed elastically resilient around a center position for the adaption of the thumb-element 24. Also the pinky-element 25 comprises its own elastically resilient finger-element adaptor 23.

A thumb-element 24 with the according finger element adaptor 22 is in addition shown in FIG. 4a to d in detail in different positions. FIGS. 4a and b show positions with straightened finger element support 22, whereas FIGS. 4c and d each show a bended position of the finger element adaptor. Therefore, the finger element adaptor comprises a motoric driven hinge connection that conceptually corresponds preferably to a first hinge connection between the carrier component 1 and the first phalanx 5. The hinge connection 22 in the shown embodiment encloses consequently its own drive housing 26 (corresponding to the first phalanx) with a motoric drive with threaded screw and gear segment 27 around a rotation axis 28 as well as a connection platform 29 for the carrier components 1 of the thumb-element 25 (cf. FIG. 4a).

The conception of the finger elements in the shown embodiments allows an adaption to the specific use case singularly by an exchange of the fingertip 18 and for a use in a hand-prosthesis of the thenar element 19 as well as the elastic adaptor 21. In addition the finger element adaptors 22 and 25 according to FIGS. 3a and b as well as FIG. 4a to d are exclusively made of components of the finger element. The drive housing 26 is with all of its build-in parts identical in construction with the first phalanx 5, the connection platform 29 with the carrier component 1. That abets a standardization of the components or entire assemblies, which in return abets an economic production and storage as well as an adaption to individual needs of the carrier of the prosthesis significantly.

An optic casing of the finger element or the entire hand-prosthesis for instance by a glove is not shown in the figures. A preferred glove made of an elastomeric material like for instance of silicon rubber has not only optical advantages in view of a textile or leather glove, but provides a better protection against pollution.

LIST OF REFERENCE SIGNS

1 Carrier component
2 first hinge axis
3 Gear segment
4 Cog segment
5 First phalanx
6 Second phalanx
7 Second hinge axis
8 Spring bar connections
9 Bearing bore at the carrier component
10 Bearing bore at the second phalanx
11 Motoric drive
12 Drive shaft
13 Threaded screw
14 Guidance
15 Core
16 Deflector
17 Slide face
18 Fingertip
19 Thenar element
20 Link component
21 Elastic adaptor
22 Thumb element adaptor
23 Pinky-element adaptor
24 Thumb-element
25 Pinky-element
26 Drive housing
27 Gear segment
28 Rotation axis
29 Connection platform

The invention claimed is:

1. A finger element, comprising:
   a) a carrier component,
   b) a first phalanx with a first hinge connection to the carrier component,
   c) a second phalanx with a second hinge connection to the first phalanx,
   d) a servo drive for the first hinge connection with a motor with a drive shaft and a worm gearing with a threaded screw and a cog segment that engages to the threaded screw, and
   e) a coupling mechanism between the first hinge connection and the second hinge connection, wherein
   f) the threaded screw is supported on the drive shaft form fittingly and axially movable as well as guided in axial direction by separate guidances.

2. The finger element according to claim 1, wherein the motor and the threaded screw as well as the guidances are arranged in the first phalanx and the cog segment is connected to the carrier component.

3. The finger element according to claim 1, wherein the cog segment is formed by a gear segment with a gear axis, wherein the gear axis predetermines a rotation axis of the first hinge connection.

4. The finger element according to claim 1, wherein the guidances and the threaded screw are combined to an assembly that is inserted in the first phalanx.

5. The finger element according to claim 4, wherein the assembly is inserted elastically.

6. The finger element according to claim 1, wherein the threaded screw is supported in radial direction to the cog segment in the guidances.

7. The finger element according to claim 1, wherein the coupling mechanism comprises at least an elastic connection between the carrier component and the second phalanx in parallel to the first phalanx.

8. The finger element according to claim 7, wherein the connection encloses one or two spring bar connections as pull-push-rods.

9. The finger element according to claim 1, wherein the second phalanx comprises an exchangeable fingertip.

10. The finger element according to claim 1, wherein the first and/or second phalanx encloses a tactile sensor or a resistance strain gauge for detecting tactile signals.

11. The finger element according to claim 8, wherein the spring bar connections are formed in a curved or buckled manner.

* * * * *

UNITED STATES PATENT AND TRADEMARK OFFICE
CERTIFICATE OF CORRECTION

PATENT NO. : 8,491,666 B2  
APPLICATION NO. : 13/203616  
DATED : July 23, 2013  
INVENTOR(S) : Stefan Schulz Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 254 days.

Signed and Sealed this
Eighth Day of September, 2015

Michelle K. Lee
*Director of the United States Patent and Trademark Office*